United States Patent [19]
Collins et al.

[11] 4,151,187
[45] Apr. 24, 1979

[54] INTERMEDIATES FOR PROSTAGLANDIN SYNTHESIS

[75] Inventors: Paul W. Collins, Deerfield; Raphael Pappo, Skokie, both of Ill.

[73] Assignee: G. D. Searle & Co., Skokie, Ill.

[21] Appl. No.: 770,536

[22] Filed: Feb. 22, 1977

[51] Int. Cl.² ............................................. C07F 7/22
[52] U.S. Cl. ..................... 260/429.7; 260/345.9 P; 260/347.8; 260/438.1; 424/305; 560/121; 542/426; 542/413
[58] Field of Search ....................................... 260/429.7

[56] References Cited

U.S. PATENT DOCUMENTS

| | | | |
|---|---|---|---|
| 4,038,308 | 7/1977 | Strike | 260/429.7 |
| 4,061,670 | 12/1977 | Floyd et al. | 260/429.7 |

OTHER PUBLICATIONS

Corey et al., JACS 98 (1), pp. 222–224 (1976).
Chemical Abstracts 82 1254452y (1975).
Chemical Abstracts 84 31199k (1976).
J. Organometallic Chem. 109, 267, 288, 328, (1976).
J. Organometallic Chem. 53, 30–32, (1973).

*Primary Examiner*—Helem M. S. Sneed
*Attorney, Agent, or Firm*—John J. McDonnell; Michael T. Murphy

[57] ABSTRACT

Compounds of the formula

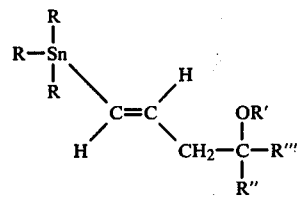

wherein R is phenyl cyclohexyl or lower alkyl containing 1–6 carbon atoms; R″ is hydrogen or methyl; R‴ is alkenyl or alkynyl having 3–5 carbon atoms; R′ is hydrogen, tetrahydrofuran-2-yl tetrahydropyran-2-yl or trialkylsilyl wherein the alkyl contains 1–4 carbon atoms. Compounds of the present invention are useful in synthesizing prostaglandin like molecules which are active anti-secretory agents.

7 Claims, No Drawings

INTERMEDIATES FOR PROSTAGLANDIN SYNTHESIS

The present invention encompasses compounds of the formula:

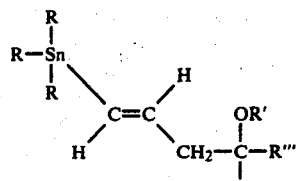

wherein R is phenyl, cyclohexyl or lower alkyl containing 1-6 carbon atoms; R" is hydrogen or methyl; R'" is alkenyl or alkynyl having 3-5 carbon atoms; R' is hydrogen, tetrahydrofuran-2-yl, tetrahydropyran-2-yl or trialkylsilyl wherein the alkyl contains 1-4 carbon atoms.

Preferred embodiments are compounds of the formula:

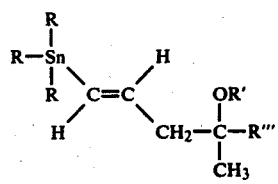

wherein R and R' are as previously defined and wherein R'" is butenyl or butynyl such as 4-methyl-4(RS)-triethylsilyloxy-oct-5-en-trans-1-enyl-tri-n-butyltin and 4-methyl-4(RS)-triethylsilyloxy-oct-5-yn-trans-1-enyl-tri-n-butyltin.

The intermediates of the present invention are converted into biologically active prostaglandins as shown in the following reaction scheme:

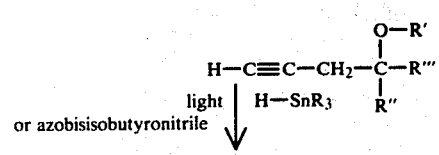

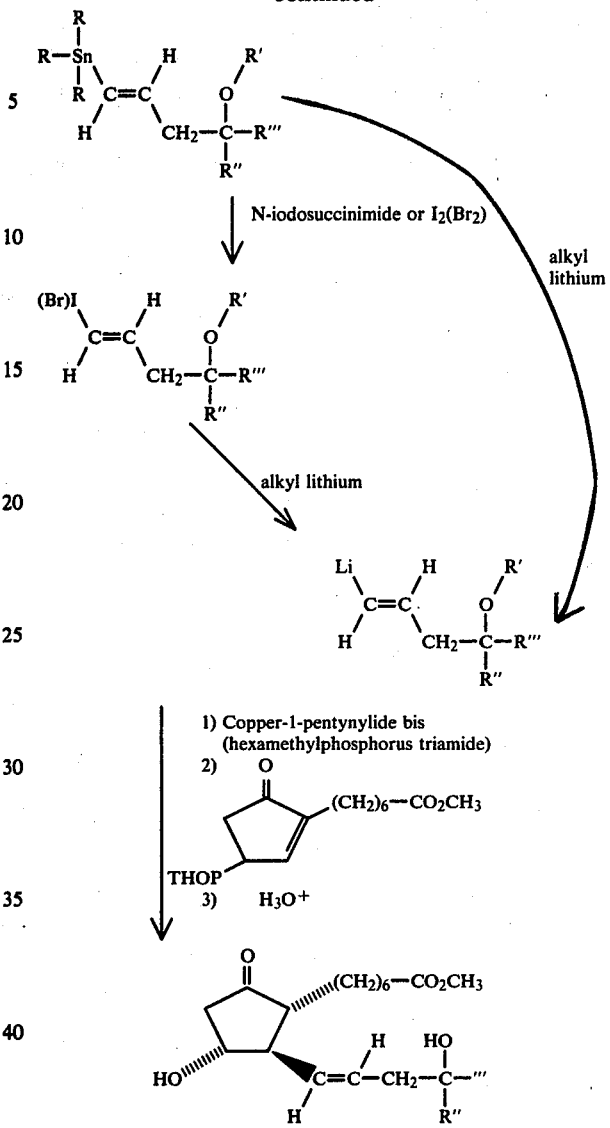

wherein R, R', R", and R'" are as previously defined.

It is particularly noted that the organo tin compound can be directly converted to the lithium intermediate without first forming the bromide or iodide. The intermediate of the present invention is also advantageous in that the $R_3SnH$ unexpectedly adds selectively to the terminal acetylene in the presence of other unsaturation.

Corey et al., J. Am. Chem. Soc. 98, 223(1976) describes compounds of the formula:

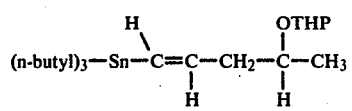

THP = tetrahydropyran

Compounds of the present invention are particularly distinct in that an ethynylene or vinylene is further contained in the side chain.

Compounds of the present invention are intermediates for the preparation of prostaglandin like compounds which display valuable pharmacological properties as is exemplified by their ability to inhibit the gastric secretion stimulated by secretogogues such as histamine and pentagastrin.

The specific assay used to detect gastric antisecretory activity is described as follows:

Adult female beagle dogs weighing 13-20 kg. are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1 N sodium hydroxide to pH 7.0. Following a 30 minute basal secretion the dogs are infused with a saline solution of histamine dihydrochloride at a dose of 1.0 mg/hr. The volume of the diffusion is kept at approximately 13 ml/hr. A steady state plateau of gastric secretion is obtained approximately 1 hour following the start of histamine infusion, at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

The compounds prepared from intermediates of the present invention are combined with common pharmaceutical carriers and administered to animals in need of antisecretory treatment. For example, propantheline bromide described in Cuttings Handbook of pharmacology, 4th edition, Appleton-Century-Crofts, N.Y., N.Y., page 548, is active in the above test.

The invention will appear more fully from the examples which follow. The examples are given by way of illustration only and are not to be construed as limiting the invention either in spirit or in scope as many modifications both in materials and methods will be apparent to those skilled in the art. In these examples temperatures are given in degrees centigrade (° C.) and quantities of materials in parts by weight unless otherwise noted.

EXAMPLE 1

To a solution consisting of 6.06 parts of magnesium, 15 parts by volume of ether and 0.06 part of mercuric chloride, stirred at room temperature in an atmosphere of nitrogen, was added 0.5 part by volume of a solution consisting of 29.74 parts of propargyl bromide and 70 parts by volume of ether. The resulting mixture was then cooled to $-10°$ to $-15°$ and the remaining propargyl bromide solution was slowly added over a period of 45 minutes. At the end of the addition period, stirring was continued at $-10°$ for about 15 minutes longer. To that mixture was then added, with stirring, over a period of 45 minutes at $-3°$ to $-5°$, a mixture consisting of 22 parts of 3-hexyn-2-one and 60 parts by volume of benzene. At the end of the addition period, stirring was continued for about 20 minutes at $-3°$, and the reaction mixture was then poured carefully into cold dilute sulfuric acid. The aqueous phase was separated, extracted with ether and the combined ether extracts were washed with water, dried over anhydrous sodium sulfate and evaporated to dryness. Vacuum distillation of the residue afforded 4-methyl-1,5-octadiyn-4(RS)-ol, characterized by infrared absorption maxima of about 3620, 3330, 2250, 1385, 1355, 1085, 940, and 770 cm.$^{-1}$.

A mixture consisting of 1.25 parts of 4-methyl-1,5-octadiyn-4(RS)-ol, 1.5 parts of triethylsilyl chloride, 2.5 parts by volume of dimethylformamide and 1 part by volume of triethylamine was stirred in an atmosphere of nitrogen at room temperature for about 24 hours. The mixture was then poured into benzene and diluted with water. The layers were separated and the organic layer was washed successively with dilute hydrochloric acid, water and saturated aqueous potassium bicarbonate, dried over anhydrous sodium sulfate and the solvent was removed under reduced pressure. Adsorption of the residue on a silica gel chromatographic column followed by elution with hexane afforded 4-methyl-1,5-octadiyn-4(RS)-ol triethylsilyl ether.

0.250 Part of this compound is treated with 0.335 part of tri-n-butyltin hydride at 0° C. under UV light for 2 hours to provide 4-methyl-4(RS)-triethylsilyloxy-oct-5-yl-trans-1-enyl tri n-butyltin, having the formula:

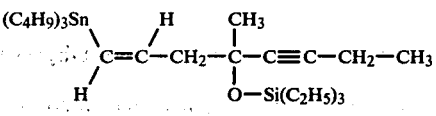

0.250 Part of this tin compound is dissolved in 2.5 part by volume of tetrahydrofuran and cooled to $-50°$ C. and then treated with 0.19 part of N-iodosuccinimide in 1 part by volume of tetrahydrofuran. After about 25% of the N-iodosuccinimide is added, the reaction is allowed to warm to $-20°$ C. and the addition is completed.

The reaction mixture is then diluted with hexane and washed with dilute sodium sulfite solution. The reaction mixture is further washed with saturated EDTA solution three times, water, and then the solvent is removed in vacuo. Distillation under high vacuum provides 4-methyl-4(RS)-triethylsilyloxy-oct-5-yn-trans-b 1-enyl iodide, boiling at 100°-128° C.

3 Parts of this iodide is desolved in 20 parts by volume of dry ether and cooled to $-55°$ C. and then treated with 3.8 parts by volume of 2.14 molar solution of n-butyl lithium. The reaction mixture is cooled to $-60°$ C. and a solution of 3.6 parts of copper 1-pentynylide bis-hexamethylphosphorous triamide (prepared from 1.04 parts of copper pentynylide and 2.56 parts of hexamethyl phosphorous triamide) in 18 parts by volume of ether is added and the resulting solution is stirred at $-60°$ C. for 15 minutes.

Alternately the vinyl tin compound (5.03 parts) in 25 parts by volume of tetrahydrofuran at $-40°$ C. is reacted with 4 parts by volume of 2.5 molar butyl lithium and the resulting product is converted to the above organo copper reagent.

1.28 Parts of methyl 7-[3(RS)tetrahydropyran-2-yloxy-5-oxocyclopent-1-ene]heptanoate dissolved in 8 parts by volume of ethyl ether is added to the above copper reagent. The reaction mixture is stirred at $-45°$ C. for 1½ hours.

The reaction mixture is treated with cold dilute hydrochloric acid and the organic and aqueous layers are separated. The organic layer is washed with water, filtered, dried, and the solvent stripped. The product is hydrolysed with a solution of 3 parts of acetic acid, 1 part water and 1 part tetrahydrofuran at room temperature overnight. The solvent is removed by distillation at 28°-34° C. and the residual oil is diluted with benzene and washed with potassium bicarbonate and water, dried, and the solvent is removed. Chromatography of the residual oil on silica gel with 100% ethyl acetate as eluent provides racemic methyl [3(α)-hydroxy-2β-(4(R)-hydroxy-4-methyl-trans-1-octen-5-ynyl)-5-oxocyclopentane]-1α-heptanoate

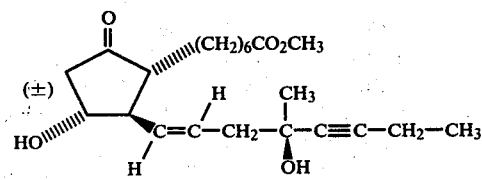

and racemic methyl [3(α)-hydroxy-2β-(4(S)-hydroxy-4-methyl-trans-1-octen-5-ynyl)-5-oxocyclopentane]-1α-heptanoate.

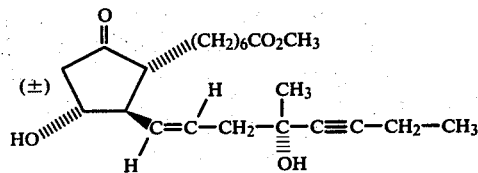

EXAMPLE 2

Treatment of 1.224 parts of 4-methyl-1,5-octadiyn-4(RS)-ol with 0.457 parts of lithium aluminum hydride in tetrahydrofuran provides 4-methyl-1-octyn-trans-en-4(RS)-ol.

Following the procedures set out in Example 1 provides 4-methyl-4(RS)-triethylsilyloxy-oct-5-trans-en-trans-1-enyl tri n-butyltin, having the formula:

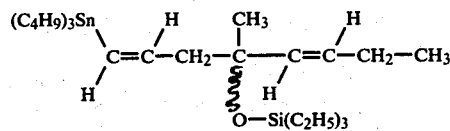

This compound is a useful intermediate in preparing biologically active prostaglandins of the formula:

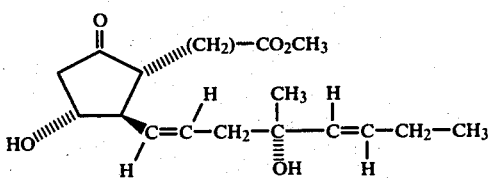

and the corresponding 16(R) hydroxy derivative.

EXAMPLE 3

Replacing tri-n-butyl tin hydride with an equivalent quantity of triphenyl tin hydride in the procedure in Example 1 provides 4-methyl-4(RS)-triethylsilyloxy-oct-5-yn-trans-1-enyl triphenyl tin, having the following structural formula:

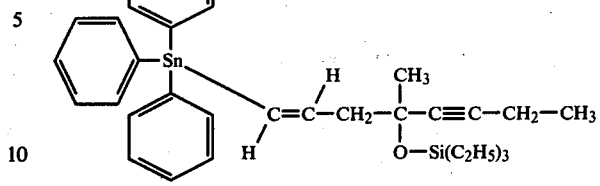

EXAMPLE 4

4-Methyl-1,5-octadiyn-4(RS)-ol is reacted with dihydropyran in the presence of p-toluenesulfonic acid in dry benzene to provide 4-methyl-4(RS)-tetrahydropyran-2-yloxy-1,5-octadiyne which in turn is reacted with triethyl tin hydride to provide 4-methyl-4(RS)-tetrahydropyran-2-yloxy-oct-5-yn-trans-1-enyl triethyl tin, having the following structural formula:

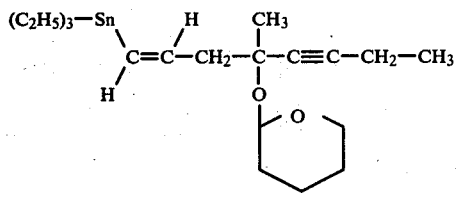

Replacing dihydropyran with dihydrofuran provides 4-methyl-4(RS)-tetrahydrofuran-2-yloxy-oct-5-yn-trans-1-enyl triethyl tin having the formula:

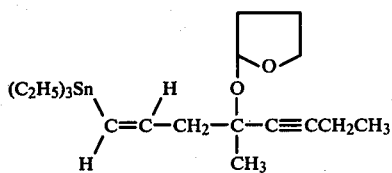

EXAMPLE 5

1,5-Octadiyn-4(RS)-ol is reacted with 1 equivalent of tri-n-butyl tin hydride to provide 4-hydroxy-oct-5-yn-trans-1-enyl tri-n-butyl tin, having the following structural formula:

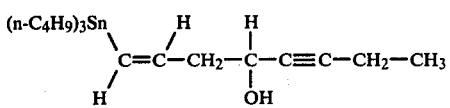

EXAMPLE 6

Following essentially the procedure set out in Example 1 and beginning with 4-hexyn-2-one, 4-methyl-4(RS)-trimethylsilyloxy-oct-6-yn-trans-1-enyl tri n-butyltin, having the formula

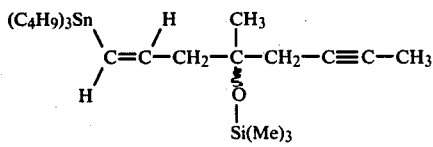

which in turn is converted to racemic methyl-[3(α)hydroxy-2β-(4(RS)-hydroxy-4-methyl-trans-1-octen-6-ynyl)-5-oxocyclopentane]-1α-heptanoate, having the formula:

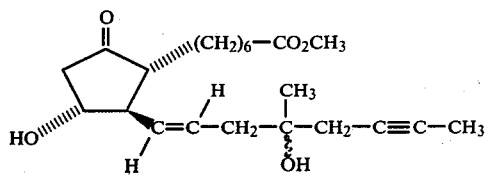

EXAMPLE 7

Following essentially the procedure set out in Example 1 and beginning with 4-cis-hexen-2-one provides 4-methyl-4(RS)-trimethylsilyloxy-oct-6-cis-en-trans-1-enyl tri n-butyltin, having the formula

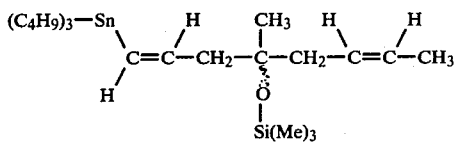

which in turn is converted to racemic methyl-[3(α)hydroxy-2β-(4(RS)-hydroxy-4-methyl-trans-1-octen-6-cis-enyl)-5-oxocyclopentane]-1α-heptanoate, having the formula

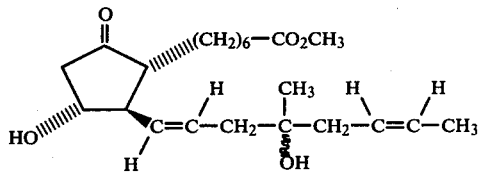

EXAMPLE 8

Following essentially the procedure set out in Example 1 and beginning with 5-hexen-2-one provides 4-methyl-4(RS)-trimethylsilyloxy-oct-7-en-trans-1-enyl tri n-butyltin

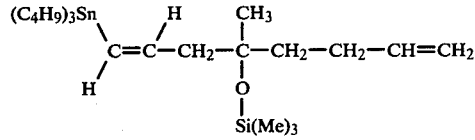

which in turn is converted to racemic methyl-[3(α)hydroxy-2β-(4(RS)-hydroxy-4-methyl-trans-1-octen-6-cis-enyl-5-oxocyclopentane]-1α-heptanoate, having the formula

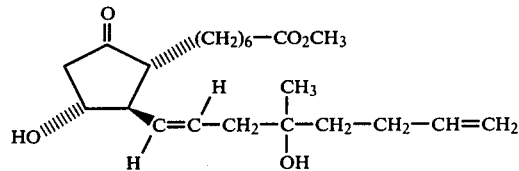

EXAMPLE 9

Replacing tri-n-butyl tin hydride with an equivalent quantity of tricyclohexyl tin hydride in the procedure in Example 1 provides 4-methyl-4(RS)-triethylsilyloxy-oct-5-yn-trans-1-enyl tri-cyclohexyl tin.

EXAMPLE 10

15 Parts of 4-hydroxy-4-methyl-1,5-dioctyne are dissolved in 150 parts by volume of ethyl ether and cooled to −60° C. Then 101 parts by volume of 2.5 molar butyl lithium in 62 parts by volume of ethyl ether is slowly added over one half hour period at −60° C. After completion of the addition the mixture is stirred at −60° C. for one half hour and then at 0° C. for 1 hour at which time the mixture becomes a gel.

35.0 Parts of trimethylsilylchloride in 300 parts by volume of ethyl ether is added over one half hour at 0° C. and the gel dissolves. After about 20 minutes at room temperature a white precipitate appears and the reaction mixture is stirred at room temperature for an additional hour.

The reaction mixture is diluted with ether and water. The layers are separated and the etheral layer is washed with water, dried over anhydrous sodium sulfate, and the solvent is removed. This procedure provides 4-methyl-1-trimethylsilyl-1,5-octadiyn-4(RS)ol trimethylsilyl ether, having the formula

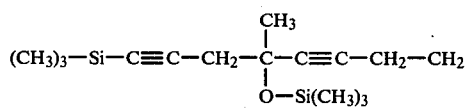

45 Parts of this product is dissolved in 1000 parts of a solution which is 3/1/1 acetic acid, tetrahydrofuran, and water. The mixture is stirred overnight and the solvent is removed by aspiration at 35°–45° C. The residue is taken up in ether-benzene and washed 3 times with dilute sodium hydroxide and water. The residue is dried over anhydrous sodium sulfate and the solvent is removed. The product is distilled under high vacuum and has a boiling point of 68°–70° C. This procedure provides the 4-hydroxy derivative of the previous compound.

2 Parts of this 4-hydroxy compound are reduced to the corresponding cis-5,6-alkene with 12 parts by volume of a zinc couple (prepared from 15.6 parts of silver acetate, 120 parts by volume isopropanol, 40 parts by volume of acetic acid followed by addition of 46.9 parts of zinc dust). The reaction was stirred and refluxed for 7 hours. The zinc was then filtered and the filtrate stripped to dryness by aspiration at 30°–35° C. The residue was diluted with benzene and water. The layers were separated and the organic layer washed with water, potassium carbonate, water, and then dried and solvent removed. This procedure provides 4-methyl-4(RS)hydroxy-5-cis-en-1-octynyl trimethylsilane.

15 Parts of this compound are dissolved in 120 parts by volume of dimethylformamide and treated with 15 parts of potassium fluoride. This mixture is stirred at room temperature for 20 hours and the reaction is worked-up by ciluting the mixture with 500 ml hexane and washing with water to remove the dimethylformamide. The organic layer is washed with dilute hydrochloric acid to remove dimethylformamide, dried over anhydrous sodium sulfate, and the solvent removed. This provides 4-methyl-4(RS)-hydroxy-5-cis-en-1-octyne.

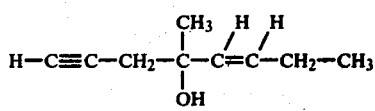

Following the procedure set out in Example 1 provides 4-methyl-4(RS)-triethylsilyloxy-oct-5-cis-en-trans-1-enyl tri n-butyltin

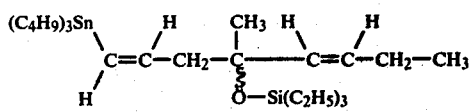

which in turn is converted to an antisecretory prostaglandin of the formula

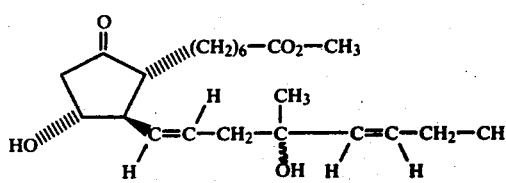

What is claimed is:

1. A compound of the formula

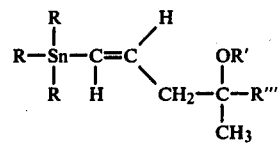

wherein R is phenyl, cyclohexyl or lower alkyl having 1–6 carbon atoms; R' is hydrogen or trialkylsilyl wherein the alkyl contains 1–4 carbon atoms; and R''' is butenyl or butynyl.

2. A compound according to claim 1 which is 4-methyl-4(RS)-triethylsilyloxy-oct-5-trans-en-trans-1-enyl-tri-n-butyl tin.

3. A compound according to claim 1 which is 4-methyl-4(RS)-triethylsilyloxy-oct-5-yn-trans-1-enyl-tri-n-butyltin.

4. A compound according to claim 1 which is 4-methyl-4(RS)-trimethylsilyloxy-oct-6-yn-trans-1-enyl-tri-n-butyltin.

5. A compound according to claim 1 which is 4-methyl-4(RS)-trimethylsilyloxy-oct-6-cis-en-trans-1-enyl tri n butyltin.

6. A compound according to claim 1 which is 4-methyl-4(RS)-trimethylsilyloxy-oct-7-en-trans-1-enyl tri n-butyltin.

7. A compound according to claim 1 which is 4-methyl-4(RS)-triethylsilyloxy-oct-5-cis-en-trans-1-enyl tri n-butyltin.

* * * * *